(12) United States Patent
Mertens

(10) Patent No.: US 8,481,942 B2
(45) Date of Patent: Jul. 9, 2013

(54) DIRECT MATCH SPECTROGRAPHIC DETERMINATION OF FUEL PROPERTIES

(75) Inventor: Daniel C. Mertens, San Antonio, TX (US)

(73) Assignee: Tesoro Refining and Marketing Company, San Antonio, TX (US)

( * ) Notice: Subject to any disclaimer, the term of this patent is extended or adjusted under 35 U.S.C. 154(b) by 114 days.

(21) Appl. No.: 13/084,500

(22) Filed: Apr. 11, 2011

(65) Prior Publication Data

US 2011/0249261 A1   Oct. 13, 2011

Related U.S. Application Data

(60) Provisional application No. 61/322,755, filed on Apr. 9, 2010.

(51) Int. Cl.
*G01N 21/00* (2006.01)
*G01J 5/02* (2006.01)
*G01J 3/28* (2006.01)
*G01J 5/00* (2006.01)

(52) U.S. Cl.
USPC ............... 250/338.5; 250/339.07; 250/338.1; 356/326

(58) Field of Classification Search
USPC ............. 250/338.1, 339.07, 339.12; 356/326
See application file for complete search history.

(56) References Cited

U.S. PATENT DOCUMENTS 5,822,058 A    10/1998   Adler-Golden et al.
2004/0033617 A1   2/2004   Sonbul

OTHER PUBLICATIONS

PCT International Search Report for PCT/US11/31996 filed on Apr. 11, 2011.

*Primary Examiner* — David Porta
*Assistant Examiner* — Faye Boosalis
(74) *Attorney, Agent, or Firm* — Cox Smith Matthews Incorporated

(57) ABSTRACT

A method and apparatus for deriving refinery product property value based on data produced from a globally-calibrated spectrographic analyzer and data from a non-spectrographic analyzer.

19 Claims, 6 Drawing Sheets

DIRECT MATCH SPECTROGRAPHIC DETERMINATION OF FUEL PROPERTIES

CROSS-REFERENCE TO RELATED APPLICATION

This application claims priority to U.S. Provisional Patent Application 61/322,755 entitled "Direct Match Spectrographic Determination of Fuel Properties" filed Apr. 9, 2010, which is hereby entirely incorporated herein by reference.

FIELD

The disclosed method and apparatus generally relate to spectrographic determination of fuel properties.

BACKGROUND

Hydrocarbons, such as crude oil, may be refined to produce various products, such as jet fuel, gasoline, diesel fuel, paraffins, kerosene, naphtha, lubricating oils, asphalts, fuel oil, and liquefied petroleum gases (LPGs) such as propane and butane. Refining generally refers to a group of processes that treat and chemically change hydrocarbons. The refining process for crude oil generally breaks apart the heavier, or more dense, hydrocarbon chains of the crude oil at various pressures and temperatures to produce lighter, or less dense, hydrocarbon fractions. The refining process may result in finished products, such as diesel fuel, and may result in intermediate products, such as fuel oil, that require further processing to produce a finished product. For example, a fuel oil may be refined further through conversion to change its chemical components in a way suitable for use in blending gasoline.

Crude oil may be made up of hundreds of chemical components. Such components may include, for example, alkanes, aromatics, olefins, isomers, and napthenes. Some of those components are heavier than others, and the conversion process may make some components heavier, or may make them lighter, or may change them in some other way to result in certain properties. The conversion process may include, for example, distillation, coking, hydrocracking, fluidized catalytic cracking (FCC), alkylation, de-sulfurization, reforming and isomerization. The conversion process may also rely on catalysts, such as platinum, and other process variables, such as temperature and pressure to effect conversion. Thus, product components may change during the refining process. The refining process may also include blending various intermediate products and additives to create a finished product. Additives may include, for example, ethers and alcohols.

Each product may have various chemical and physical properties that particularly relate to that product's usefulness. Some of those properties may be related to a particular components such as benzene. Other properties may be related to the product overall, such as specific gravity. For example, increasing octane may be useful in reducing engine "knocking" when burned, and reducing sulfur may result in lower levels of harmful sulfur dioxide, a combustion by-product.

Petroleum products may be produced to specification. Thus, a refinery in a certain geographic location may develop a product matrix to meet a certain specification based on the types of crude oil that it processes. For example, a retail gasoline station in the northwestern United States may request gasoline blended to have a certain grade, such as regular, or be of a certain type, such as RFG (ReFormulated Gasoline), and be suitable for a certain season, such as winter. A refiner may then develop a product matrix for its location that may characterize the requested grade, type and season. To develop a certain gasoline blend, a refinery may mix various intermediate products, such as those from a vacuum tower, hydrocracker, FCC unit and/or alkylation unit. Different matrices may be provided for other products, and those matrices may vary in complexity. For example, a product matrix for diesel fuel may characterize different components than a gasoline product matrix.

Additionally, petroleum products must comply with the environmental and other regulations of the state in which the product will be sold and used. For example, an environmental regulation may require reduced sulfur in the finished product.

Thus, prior to sending a product to a retailer for sale, a refinery may test or analyze the finished product and/or intermediate products (such as, for example, blendstock for oxygenate blending, or BOB) to determine the properties of the products and to verify those properties against the product specification and regulatory standards. Industry standards, such as ASTM standards, may in some cases define how such tests or analyses are conducted, and often, regulatory agencies will rely on industry standard test procedures to certify a product for sale or use.

Spectrographic analyzers having location- and matrix-specific calibrations may be used by refineries to determine product properties. However, because such calibrations may be location- and matrix-specific, methods using spectrographic analyzers may not comply with the requirements of existing industry standard methods of certifying a fuel product as having specific properties. Regulatory agencies may thus refuse to accept test results based on spectrographic analysis as valid for product certification. In addition, location- and matrix-specific calibrations may make it difficult to compare data between different instruments, sampling or processing techniques, and laboratories, which may, for example, be physically located at the same or different location. For example, a refiner may have multiple refineries in different geographic locations, each processing a different crude oil and using different instruments. Therefore, there is a need for a method and apparatus for standardizing product property values determined by spectrographic analysis.

SUMMARY

A method for deriving a refinery product property value, the method comprising determining a property value of a first refinery product using a non-spectrographic test; determining a property value of the first refinery product using a first globally-calibrated spectrographic analyzer; determining a property value of a second refinery product using a second globally-calibrated spectrographic analyzer; determining a difference between the spectrographically-determined property values of the first refinery product and the second refinery product; adding the difference to the non-spectrographically-determined property value of the first refinery product to derive a property value for the second refinery product.

An apparatus for direct match comparison, the apparatus comprising a spectrographic analyzer capable of receiving a property value of a first refinery product using a non-spectrographic test; determining a property value of the first refinery product using a first globally-calibrated spectrographic analyzer; determining a property value of a second refinery product; determining a difference between the spectrographically-determined property values of the first refinery product and the second refinery product; and adding the difference to the non-spectrographically-determined property value of the first refinery product to derive a property value for the second refinery product.

A system for direct match comparison, the system comprising a (1) spectrographic analyzer capable of determining a property value of a first refinery product, and determining a property value of a second refinery product; and (2) a computer programmed to receive a property value of the first refinery product, the property value determined using a non-spectrographic test; receive the property values of the first and second refinery products determined by the spectrographic analyzer; determine a difference between the spectrographically-determined property values of the first refinery product and the second refinery product; and add the difference to the non-spectrographically-determined property value of the first refinery product to derive a property value for the second refinery product.

An apparatus for direct match comparison, the apparatus comprising a computer programmed (A) to receive (1) a property value of a first refinery product, the property value determined using a non-spectrographic test, (2) a property value of the first refinery product determined using a spectrographic analyzer, and (3) a property value of a second refinery product determined using the spectrographic analyzer; (B) to determine a difference between the spectrographically-determined property values of the first refinery product and the second refinery product; and (C) add the difference to the non-spectrographically-determined property value of the first refinery product to derive a property value for the second refinery product.

DETAILED DESCRIPTION

Figure 1:
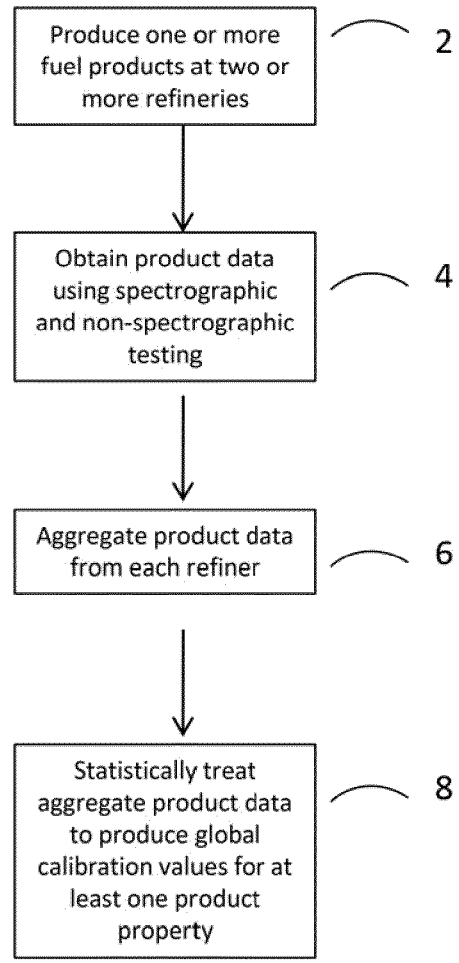
FIG. 1 depicts one embodiment of a method for producing global calibration data.

Spectrographic analyzers, or spectrometers, may include, for example, those associated with the following wavelengths or techniques: Near Infrared (NIR), Mid Infrared (MIR), Near and Mid (full range) Infrared (IR), Fourier Transform Near Infrared (FTNIR), Fourier Transform Mid Infrared (FT-MIR), Fourier Transform Near and Mid (full range) Infrared (FTIR), Nuclear Magnetic Resonance (NMR) and Raman. By way of nonlimiting example, such an analyzer may be a stand-alone instrument suitable for batch testing, such as those produced by ABB Bomem, and by Analect or may be an on-line instrument (i.e., connected to fuel production equipment) suitable for in-stream testing, such as those produced by ABB Bomem, and Analect. Such an analyzer may be implemented in hardware and/or software.

Spectrographic analyzers may be used to quantify properties of for example, lubricants (nominally lubricating oils), spark ignition fuels (nominally gasoline), turbine fuels (nominally jet fuel), and distillate fuels (nominally diesel fuel and home heating oils.). Use of such analyzers may achieve an improved precision (e.g., less test variation) when compared to other available industry techniques, such as engine testing.

A refinery may calibrate the spectrographic analyzer to the product properties. For example, the properties of fuels may include, but are not limited to those shown in Table 1:

TABLE 1

| Property | Spark Ignition fuel (e.g. Gasoline) | Turbine Fuel (e.g. Jet) | Compression Ignition Fuel (e.g. Diesel) | Distillate Fuels (e.g. Htr Oil) |
|---|---|---|---|---|
| RON | x | | | |
| MON | x | | | |
| RVP | x | | | |
| $T_{v/l-20}$ | x | | | |
| Specific Gravity | x | x | x | x |
| Aromatics | x | x | x | |
| Polynuclear Aromatics | | | x | |
| Olefins | x | | | |
| Benzene | x | | | |
| Oxygen | x | | | |
| Ethanol | x | | | |
| Distillation | x | x | x | x |
| Flash | | x | x | x |
| Viscosity | | x | x | x |
| Analine Point | | x | | |
| Cetane Number | | | x | |

"RON" refers to Research Octane Number.
"MON" refers to Motor Octane Number.
"RVP" refers to Reid Vapor Pressure.
$T(v/l) = 20$ refers to the temperature at which the vapor to liquid ratio equals 20.
Distillation properties may be obtained with respect to IBP, T10, T30, T50, T70, T90, EP, E200 and E300, for example.

To calibrate a spectrometer to a product's properties and property values, a refinery may take multiple samples of particular product over time, and send a first portion of each sample to a laboratory for primary (non-spectrographic) testing, e.g., engine testing, according to ASTM standards, such as ASTM D2700 for testing motor octane number (MON) of spark-ignition engine fuels. The refinery may run a second portion of each sample through the spectrographic analyzer to generate spectral data, and compare the primary test data to the spectral data in order to correlate product properties and property values to the spectral data. For example, a refinery may determine the relationship between an engine test MON value of a sample against that sample's wavelength absorption data. Each comparison generates calibration data. A refinery may aggregate the data and use statistical tools to calibrate the spectrographic analyzer to specific product property values. For example, a refinery may use a multivariate regression analysis, such as that specified in ASTM E1655, to develop a calibration curve from the calibration data. After calibration, a refinery may use the spectrographic analyzer to analyze the properties of a product sample and predict property values without having to also analyze the sample using primary or non-spectrographic testing.

Although using a spectrographic analyzer may provide a more precise result, product matrix biases, or the non-linearity of various product properties, can adversely affect the accuracy of the property value measurements. These adverse biases may be addressed by creating location-specific and matrix-specific calibrations. For a gasoline blend, for example, a product matrix may be dependent upon the refinery location, gasoline grade (e.g., regular/premium), gasoline type (e.g., RFG (ReFormulated Gasoline), RBOB (Reformulated Blendstock for Oxygenate Blending), Conventional, CARB (California Air Resources Board), CARBOB (California Air Resources Blendstock for Oxygenate Blending)), and season (e.g., Winter, Summer). A refinery could thus have several separate calibrations that would cover all or some of its specific types, grades and seasons of gasoline, and these calibrations would generally only include data from that specific refinery (or its laboratory), and may not include data from other refineries (or outside laboratories). A refinery may similarly develop calibrations for other intermediate and finished products, as well.

Creating and using location-specific and matrix-specific calibrations may raise a number of challenges, such as a general lack of confidence that after the calibration is created, any property value will be measured accurately (extrapolation). Another challenge may be that the predicted value may be difficult to replicate at refineries or laboratories in other locations that process and test other products. A further challenge may be a lack of acceptance of property values for certification by an industry group or regulatory agency.

Furthermore, a product may be developed to have certain property values, and may be certified on the basis of certain property values. Certain property values such as research octane number (RON) and motor octane number (MON) may, for example, indicate how a fuel may behave in operation, such as when burned in an engine. However, some refineries may optimize the RON and MON (and other property values) in different ways, including, for example, by addition of different ratios of blending components or by processing different crude oils or other intermediate products. Thus, different products may have the same property values, but may show significantly different chemical signatures when analyzed by a spectrographic analyzer.

One way to resolve location- and matrix-specific biases may be to generate global calibration values. A global calibration may be based on spectral and analytical data from a variety of location- and matrix-specific calibrations. "Global" may refer to worldwide refinery product, or as much refinery product as may be available from participating refineries. In some embodiments, global calibration data may be produced from a data set of participating users, and may include for example, data produced from a range of blend components, fuel properties or a combination of both. The global calibration values may be based on location- and matrix-specific data for a particular product, such as gasoline, produced by a variety of refineries, or may be based on a variety of products from one or more refineries. Global calibration data for gasoline, for example, may include data from a variety of locations and from a variety of product matrices. A group of refineries may aggregate their location- and matrix-specific calibrations, and use a statistical tool to develop global calibration values. For example, a multivariate regression analysis, such as that described in ASTM E1655, may be used to develop global calibration values for various properties.

In some embodiments, spectral data that is included in global calibration may be associated with a region of the spectrum where one or more species that may be present in a fuel are vibrationally active, e.g., where such species may experience one or more molecular oscillations. In some embodiments, spectral data that is included in global calibration may be associated with a region of the spectrum where the data is related to different refineries or where the data is related to different seasonal varieties of a type of fuel. In some embodiments, a spectral region may be selected because including data from such a region may affect the spread of data included in global calibration, because inclusion of data from such regions affects the local curvature of global calibration data, or both.

FIG. 1 depicts an exemplary embodiment of a method of developing global calibration data for a refinery product comprising fuel. In step 2, two or more refineries may produce one or more fuel products, such as gasoline. Of course, other types of refinery products, such as diesel and jet fuel may be produced. Each product may have its own product matrix. For example, a refinery at one geographic location may have a gasoline product matrix characterized by grade, type and season. A refinery at a different geographic location may have a different gasoline product matrix characterized by grade, type and season.

In step 4, each refinery may test each product using non-spectrographic (e.g., engine testing, distillate testing, etc) and spectrographic testing (e.g., using a spectrographic analyzer) in order to determine product values and spectral data pertaining to each product. Of course, outside laboratories may test the refinery products for a refinery, or provide testing in addition to a refinery's own testing. Data may be determined based on each product, or on one or more matrix variables, or on one or more product properties (such as those listed in Table 2), or on the entire output of a refinery, or on any other desired basis suitable for globally calibrating a spectrographic analyzer for analyzing refinery product. Spectrographic data included for the purpose of global calibration may include data from the entire spectral region collected during spectrographic testing or may include data, e.g., such as absorption, from a more narrow spectral region.

In step 6, each refinery (or laboratory) may provide the data collected in step 4 for aggregation. For example, each refinery (or laboratory) may send its data to a spectrographic analyzer manufacturer, or to an industry group for aggregation.

In step 8; the aggregated product data may be statistically treated as discussed above in order to develop global calibration data for each refinery product. Thereafter, the global calibration data may be provided to one or more of the participating refineries, as well as to non-participating refineries and laboratories.

A manufacturer of the spectrographic analyzer may develop global calibration values, and provide such values along with its spectrographic analyzers. A manufacturer may periodically update the global calibration values as participating refineries and laboratories create or refine their location- and matrix-specific calibrations and provide that data to the manufacturer. Of course, other parties may develop global calibration values, such as industry groups, vendors, vendor groups or laboratories. Thus, each laboratory or refinery may have one or more globally-calibrated spectrographic analyzers, and those global calibrations may be the same for all refineries and laboratories using a particular manufacturer's equipment.

However, using global calibration values to determine property values of a particular product at a particular refinery requires compensating for location- and matrix-specific biases. To do so, a refinery may develop a reference product and use a direct match technique to correct such biases.

By way of example, a reference product comprising a fuel may be used. A reference fuel may be collected as a sample. The reference fuel collected may have a composition including matrix components that is related to the refinery from which it is collected. The reference fuel may then undergo primary testing using a non-spectrographic instrument or analyzer to determine the reference fuel's property values. For example, a reference fuel may be captured at a specific refinery by carefully collecting and storing a volume of fuel representative of that refinery's spark ignition fuel or blendstock, such as gasoline, of a specific grade, type and season. The octane values of the sample may then be tested by engine testing to determine a robust value for each of the properties of interest to the refinery. The octane values determined by engine testing may be statistically treated to develop a reference value for each octane value. A statistical treatment may involve, for example, using the GESD technique in accordance with ASTM Research Report D02-1481, and assess all non-rejected data for normality at a 1% significance level in accordance with the Anderson-Darling technique in Standard Practice D6299.

Of course, as noted above, other types of primary testing may be used to determine a reference fuel's property values. Other types of products, such as diesel fuels, may undergo primary testing based on other standards, such as distillate testing under ASTM D86. Other primary tests may rely on, for example, RVPe testing under ASTM D5191, and benzene testing by gas chromatography under ASTM D3606. Other non-spectrographic techniques suitable for primary testing of fuel property values may be used.

Figure 2:
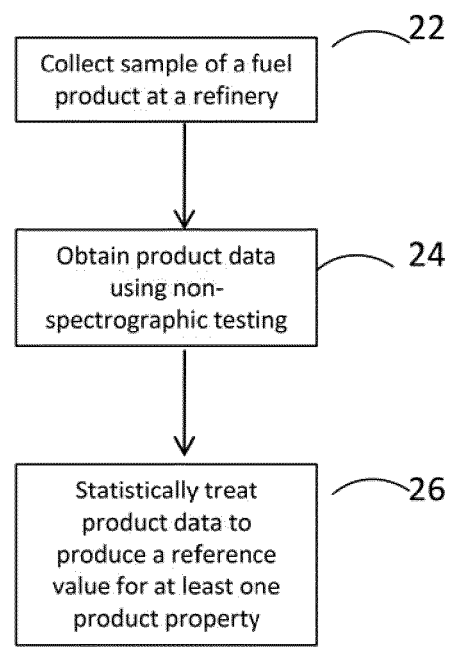
FIG. 2 depicts one embodiment of a method for determining a reference value.

FIG. 2 illustrates an exemplary method 20 of determining the reference value of a fuel. In a step 22 of FIG. 2, a refinery may collect a sample of fuel to be used as a reference. In step 24, a refinery may perform primary or non-spectrographic testing on the reference sample to obtain product data. Alternatively, as discussed in more detail below, a refinery may send out the sample for testing by an outside laboratory if a more rigorous approach is desired. In step 26, a refinery may statistically treat the product data as discussed above to produce a reference value for at least one product property.

In some embodiments, a refinery may choose among three levels of rigor in primary testing to determine reference values: laboratory reference values, consensus reference values and semi-consensus reference values. Of course, reference values may be developed in other ways. Those levels may provide a trade-off between assurance of accuracy vs. time and expense. One level of rigor may simply be a laboratory reference value determined by tests run at the refiner's own laboratory. Generally, a laboratory reference value may be determined from two or more tests done at the refinery's own laboratory. For this level, the refinery may run 20 tests on portions of the same sample of reference fuel, and determine the robust mean average of the test data. In other embodiments, a robust laboratory reference value may be determined by taking the robust mean average of data from at least 16 individual tests run within that refinery's laboratory, using as many different analyzers and technicians as possible.

To determine the accuracy of laboratory reference values, a refinery may use inter-laboratory cross-check data to verify that the reference analyzer(s) are unbiased against other laboratories. This may be accomplished by statistical quality control (SQC) charting the difference between the reference sample analyzer test data and outside laboratory test data to assure accuracy. Robust SQC charting may be used to determine, at the 2-sided 5% level, whether there is any significant bias between the reference sample analyzer data and outside laboratory data.

To calculate a laboratory reference value, a refinery may, for example, assess all candidate data (e.g., excluding statistical outliers) using the GESD technique in accordance with ASTM Research Report D02-1481, and assess all candidate data for normality at a 1% significance level in accordance with the Anderson-Darling technique in Standard Practice D6299. The calculation may involve tabulation of all the non-rejected data, determining the mean average of the non-rejected data, and determining the standard deviation of all the sample data. The reference value and standard deviation may be specified to a useful numerical precision. For example, the following values may be reported with the following precision:

| | |
|---|---|
| RON: | XX.XXX |
| MON: | XX.XXX |
| S.G at 60 F.: | X.XXXXX |
| RVP (ptot): | XX.XXX |
| $T_{v/l=20}$: | XXX.X |
| Aromatics": | XX.X |
| Olefins: | XX.X |
| Benzene: | X.XX |
| Ethanol vol %: | XX.X |
| Oxygen wt %: | X.XX |
| Distillation points: | XXX.X |

Anti-knock index (AKI) or Road Octane may be determined by the mean average of RON and MON, and then rounded down to the nearest 0.5 octane number.

Other reference values may be further calculated based on the determined value. For example, ASTM, EPA or CARB RVPe may be calculated from the PTOT value defined in ASTM D5191.

A higher level of rigor may involve developing a consensus value. Generally, a consensus value may be determined from two or more tests done at one or more outside laboratories. A consensus value may be determined by sending portions of the reference sample to, e.g., 20 different laboratories for analysis. A robust mean average of the test data from those laboratories may be used to develop a consensus value for each property of interest.

For example, a consensus value for a reference fuel may be the mean average of data from at least 16 individual tests, run by 20 different analyzers and 20 technicians, using a specified reference test method. For example, a reference test method may be specified for aromatics in an EPA-regulated gasoline as ASTM D5769 (GC mass spec), and for aromatics in a CARB-regulated gasoline as ASTM D5580.

To calculate a consensus value, a refinery may, for example, assess all candidate data (e.g., excluding statistical outliers) using the GESD technique in accordance with ASTM Research Report D02-1481, and assess all candidate data for normality at a 1% significance level in accordance with the Anderson-Darling technique in Standard Practice D6299. The calculation may involve tabulation of all the non-rejected data, determining the mean average of the non-rejected data, determining the standard deviation of all the sample data, and determining if two standard deviations ($2\sigma$) is within published reproducibility (R) of the reference test method. The consensus value and standard deviation may be specified to a useful numerical precision.

An intermediate level of rigor may involve developing a semi-consensus value by combining laboratory reference test data and consensus test data. Generally, a semi-consensus value may be determined from data produced from the refinery's own laboratory and from at least one outside laboratory. For example, a semi-consensus value may involve determining the numeric average of the robust mean average of data from 20 tests at the refiner's laboratory and the robust mean average of data from five tests run at five outside laboratories. The use of the robust mean of data from five outside laboratories may provide for any small corrections for accuracy.

To determine the accuracy of semi-consensus values, a refinery may use inter-laboratory cross-check data to verify that the reference analyzer(s) are unbiased against other laboratories. This may be accomplished by statistical quality control (SQC) charting the difference between the reference analyzer test data and outside laboratory test data to assure accuracy. Robust SQC charting may be used to determine, at the 2-sided 5% level, whether there is any significant bias between the reference analyzer data and outside laboratory data.

To calculate a semi-consensus value, a refinery may assess all candidate data (e.g., excluding statistical outliers) using the GESD technique in accordance with ASTM Research Report D02-1481, and assess all candidate data for normality at a 1% significance level in accordance with the Anderson-Darling technique in Standard Practice D6299. The calculation may involve tabulation of all the non-rejected data from the reference laboratory tests, determining the mean average of the non-rejected data, and determining the standard deviation of all the sample data. The calculation may involve tabulation of all the non-rejected data from the outside laboratory tests, determining the mean average of the non-rejected data, and determining the standard deviation of all the sample data. The calculation may involve determining the mean average of the reference laboratory non-rejected data and the outside laboratory non-rejected data. The reference value and standard deviation may be specified to a useful numerical precision.

The reference product sample remaining after primary testing may be carefully preserved to maintain the integrity of its chemical composition. The preserved reference sample, or portions thereof, may be later used in connection with testing a chemically-similar product having unknown property values. A refinery may thus take care in collecting and storing samples. For example, manual samples for laboratory batch analysis may be collected in accordance with ASTM Standard Practices D4057 and D5842. Samples may be taken in accordance with any other suitable technique. Stream samples for on-line analysis may be collected in accordance with ASTM with Standard Practice D4177. Sample fuels may be collected and stored opaque containers, such as an amber or dark brown glass bottle, to minimize exposure to Uv emissions from sources such as sunlight or fluorescent lamps. Alternatively, samples may be stored in clear bottles contained within boxes that prevent light exposure.

To test an unknown product against the reference product, a refinery may take a sample of a test product that is deemed to be chemically similar to the reference product. The test sample may be spectrographically tested together with a portion of the preserved reference sample under tightly controlled conditions.

Regarding chemical similarity, in some embodiments, a test product may be deemed chemically similar to the reference product based on chemical analysis. For example, chemical analysis may include characterization of the test and reference product using a spectrographic analyzer or with some other analytical instrument capable of quantitative chemical analysis. Chemically similar products may, for example, have a similar distribution of hydrocarbons such as octane, iso-octane, heptanes, other straight or branched chain hydrocarbons, or combinations thereof. It should be appreciated that comparison of the reference product and test product may in some embodiments be performed one or more times. More generally, the comparison of the reference product and test product may be performed a fewer number of times than analysis of test samples. Therefore, comparison of reference and test samples may economically include comparison of those samples using a greater number of techniques than associated with testing of test product. In some embodiments, the performance of the reference and test product in a test engine or some other non-spectrographic instrument may be used in the comparison.

In some embodiments, chemical similarity may be determined with references to particular properties, or by comparing spectral data. In comparing particular properties, for example, chemical similarity may be defined within a certain range. For example, chemical similarity based on octane may be defined as no more than ±2 octane number difference. In some embodiments, a test fuel may be deemed chemically similar to a reference fuel based on the following criteria:

RON within ±2 Octane Number,
MON within ±2 Octane Number,
RVPe within ±20.7 kPa (3.0 psia),
Specific Gravity ±0.1,
Aromatics ±10 vol %,
Olefins ±10 vol %,
T10 ±5.6° C. (20.0° F.)
T50 ±5.6° C. (20.0° F.),
T90 ±16.7° C. (40.0° F.),
EP ±16.7° C. (40.0° F.),
Wt % Oxygen ±1.0 wt %
Vol % Ethanol ±4.0 vol %.

Generally, a refinery may have prior knowledge of a product's chemical properties as a result of specifying the refining (including blending) process. A refinery may know, for example, that a premium gasoline is much different from regular gasoline because of the absence or presence of certain components, such as alcohols. In other words, different products may generally be different in composition, not just different in degree.

A chemically-similar test product and reference product may be tested together by spectrographic analysis. In the example of fuel, to certify a chemically-similar test fuel against a reference fuel, a direct match comparison technique may be used. For each certification, a portion of the preserved reference fuel sample may be obtained from a sealed container or from a piston type or water displacement system. Both the reference fuel and test fuel may be chilled in the same way prior to testing. For example, the temperature may be greater than 0° C. (32° F.) but not exceed 10° C. (50° F.). All comparisons may be accomplished using a single globally-calibrated spectrometer. Alternatively, different globally-calibrated spectrometers may be used. The reference fuel and test fuel may be tested in sequence for one or more cycles, e.g., 10 cycles.

For batch analysis of a test fuel in the laboratory, for example, the method may comprise (1) obtaining a sample of reference fuel (or prototype fuel, as discussed in more detail below) of the same type, grade and season as the fuel to be tested; (2) chilling both the reference fuel and the test fuel in the same manner and for the same length of time; (3) determining the reference fuel properties using the globally-calibrated spectrometer; (4) determining the test fuel properties using the globally-calibrated spectrometer; and (5) calculating the delta between the test fuel and the reference fuel for each property:

$$\Delta_i = TI_i - RI_i \qquad \text{(Equation 1)}$$

Where:
$\Delta_i$=difference between the spectrographically-determined property values of the test fuel and the reference fuel
$TI_i$=spectrographically-determined property value of the test fuel (text index)
$RI_i$=spectrographically-determined property value of the reference fuel (reference index)
i=a property, such as MON or RON The method may further comprise calculating the derived property of the test fuel ($T_i$):

$$T_i = \Delta_i + R_i \qquad \text{(Equation 2)}$$

Where:
- $T_i$=derived property value of the test fuel for certification
- $R_i$=property value of the reference fuel determined by primary testing (e.g., consensus value, laboratory reference value or semi-consensus value)

Thus, the direct match comparison technique may comprise adding the delta ($\Delta_i$) to the property value the reference fuel determined by primary testing ($R_i$) to establish the property value of the test fuel that may be used for certification. In various embodiments, $R_i$ may comprise the consensus value, the laboratory reference value or semi-consensus value of the reference fuel.

Figure 3:
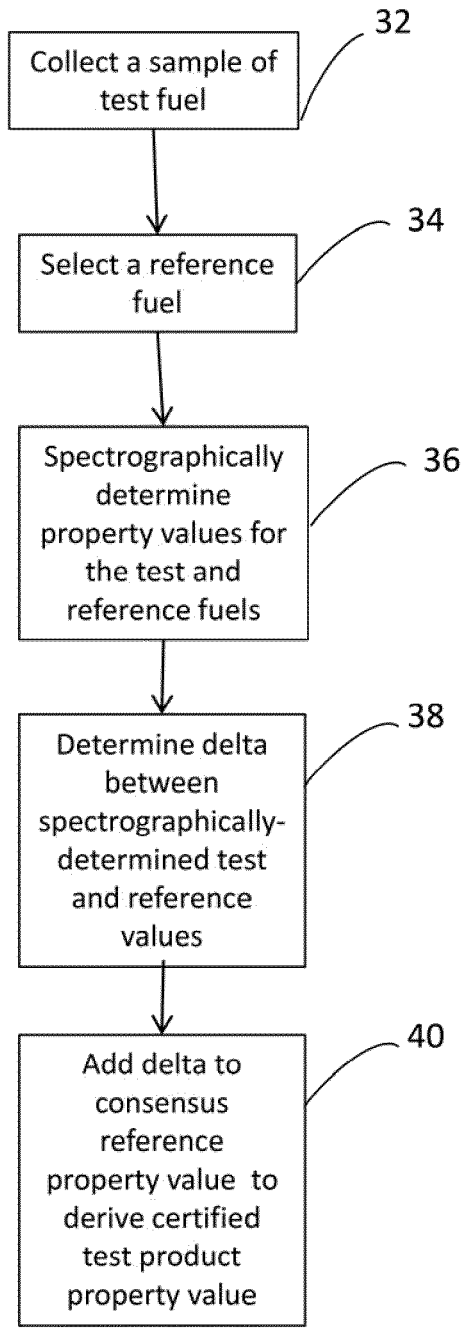
FIG. 3 depicts one embodiment of a method for direct match comparison of a test product to a reference product.

FIG. 3 illustrates an exemplary embodiment of a method for direct match comparison of a test fuel against a chemically-similar reference fuel. In a step 32, a sample of a test fuel for which analysis of a property value is desired may be collected. In a step 34, a reference fuel may be selected for use in a direct match analysis of the test fuel. The test fuel may be chemically similar to the reference fuel. Chemical similarity may be determined in the manner discussed in more detail above.

In a step 36, a refinery's laboratory may run a spectrographic test of the test fuel and the reference fuel using a globally-calibrated spectrometer. For example, as shown in Table 2, the RON for the test fuel may be determined spectroscopically to be 92.00 and the RON for the reference fuel may be determined to be spectroscopically 92.10. The MON for the test fuel may be determined to be 82.30 and the MON for the reference fuel may be spectroscopically determined to be 81.15. In step 38, the differences, or deltas, between the spectrographically-determined test and reference values may be calculated as in Table 2.

TABLE 2

| TEST | Test Fuel Spectroscopic Determination | Reference Fuel Spectroscopic Determination | Delta | Reference Fuel Consensus Value | Test Result |
|---|---|---|---|---|---|
| RON | 92.00 | 92.10 | −0.10 | 92.21 | 92.11 |
| MON | 82.30 | 81.15 | 1.15 | 82.35 | 83.50 |

Consensus values of the reference fuel may be known because the consensus values may have been previously measured such as in a manner as described in above. Of course, laboratory reference or semi-consensus values may be used, as well. For example, a consensus value for RON of the reference fuel may be 92.21 and a consensus value for MON of the reference fuel may be 82.35. In step 40, the RON and MON value deltas may be added to the reference consensus RON and MON values, respectively, to derive the RON and MON values of the test fuel suitable for certification.

For analysis of a test fuel in an on-line analyzer, for example, the method may comprise (1) lining up the correct reference (or prototype fuel, as discussed in more detail below) of the same type, grade and season as the fuel to be blended; (2) when the blend starts, testing the blender sample three times, then the reference sample once, then the blender sample three more times, all using one or more globally-calibrated spectrographic analyzers; (3) determining the average of each property of the six blender samples; (4) determine the delta between the averaged test sample property values and the reference fuel property values (using Equation 1); and (5) adding the delta to the consensus property value (or laboratory reference or semi-consensus value) of the reference fuel (using Equation 2) to derive a property value of the test fuel for certification.

The method may further comprise latching the determined property value $T_i$ for the next cycle after completing the test fuel analysis, determining the volume of gasoline that passed through the blend header since the last reported value, and integrating the property values into the total blended volume. In some embodiments, after a number of cycles, the sample test cell in the on-line analyzer may be chemically cleaned and checked with a reagent, such as toluene.

In some embodiments, the Simulated Knock Intensity (SKI) of the RON value of the test fuel may be used as a continuous indicator of the health of the on-line system. Of course, other suitable properties could be used as health indicators. The SKI may start out as the value 50 at the beginning of the blend. Depending on the condition of the sample cell and other external factors, the SKI value may be monitored through the course of the blend. Any significant deviation from the value 50 may be used to create an alarm to check the system.

Thus, for example, on the first cycle, the Simulated Knock Intensity (SKI) value may be set to 50, and the initial determined RON of the test fuel noted. On subsequent cycles, the SKI of the test fuel may be determined as follows:

$$SKI_r = 50 + \text{round}((IDO_r - DO_r)*12, 2)$$

Where:
- $SKI_r$=current simulated knock intensity of test fuel
- $IDO_r$=initial determined RON of test fuel on startup
- $CDO_r$=current determined RON of test fuel In some embodiments, acceptance criteria for on-line analysis may include ensuring that the analyzer was on-line for 95% of the blend, the RON test fuel SKIs during the blend were within ±10 SKI of the startup SKI for 90% of the blend, and desired property value conditions were met for 90% of the blend. If an on-line analyzers is be able to demonstrate significant consistency throughout a blend, as demonstrated by SQC charting, the frequency of testing the test fuel may be reduced as long as the analyzer remains demonstrably in control.

If relatively small amounts of the reference product volume are used for testing (e.g., 1 gallon/month for laboratory analysis), the reference product may be used in connection with analyzing test product. However, if the usage for testing is larger (e.g. used for an on-line analyzer) the reference product may be used to certify prototype products for use in testing test products, which in turn may be used in connection with product testing. In some embodiments, a prototype product and a reference product may be collected from the same refinery or a refinery of similar design using comparable procedures. In some embodiments, a prototype and a reference product may be collected from the same refinery or a refinery of similar design and may use a source of crude oil collected from the same geographic location. In some embodiments, a prototype product and a reference product may be processed in the same refinery or a refinery of similar design and may be processed using one or more of the same or similar additives. In some embodiments, a prototype product and a reference product may be processed in at least one common process or unit associated with the same refinery.

Generally, the reference product and prototype product may be collected in the same manner and preserved to maintain their vapor pressure and chemical stability. The collection protocol may be the same as or similar to that for collecting and preserving reference and test product. For example, a volume of reference product may comprise 200 liters packaged in 80 1-liter bottles with Teflon-lined caps, and in 480 250-ml bottles with Teflon-lined caps. For laboratory-only testing, a volume of prototype product may comprise 200 liters packaged in 800 250-ml bottles with Teflon-lined caps. For laboratory and on-line testing, a volume of prototype product may comprise 3200 liters packaged in 800 250-ml bottles with Teflon-lined caps, and comprise 2,400 liters in bulk storage in accordance with ASTM D2885 A2, and piped to on-line spectrographic analyzer.

In some embodiments, all products may be determined to be homogeneous, where representative samples are shown by be chemically the same throughout. If the reference fuel or prototype fuel is taken from a blend header during a blend, the reference fuel or prototype fuel may be taken into one large container (e.g. a capture tank,) which then could be mixed and deemed homogeneous and representative. Once the capture tank is mixed, lab samples may be collected into chilled bottles through a chiller, the fuel sample temperature brought to below 10° C. (50° F.,) and a dip tube used that reaches the bottom of the bottles to avoid agitation due to splashing. The bottles may be sealed with Teflon®-lined caps to avoid loss of vapor pressure, labeled with its representative grade, type and season and the date of capture, stored out of direct light of any kind, and kept in an environment where the temperature is no greater than 25° C. (77° F.).

If the product is to be taken from a tank or a finished product discharge pump, the recommended primary capture device may be a clean (preferably new) stainless steel drum or drums, or a portable semi-bulk container. Capturing the product may involve pre-cooling the empty drum so that its skin temperature is less than 10° C. (50° F.), filling the drum through a chiller to cool the product to less than 10° C. (50° F.), sealing the drum so as to leave approximately 2.5 cm of head space, and storing the drums in an environment where the temperature is no greater than 25° C. (77° F.). When filling from the drum(s) to bottles or to a prototype fuel tank, the bottles or tanks may be chilled and a drum pump may be used to transfer fluid from the drum to the bottles or tanks. Samples may be taken at the beginning, middle and end of the transfer process. Those samples may be tested using a globally-calibrated spectrometer to verify that the samples are homogenous.

To certify a prototype product against a reference product for which consensus values have been determined, a direct match comparison technique may be used in the same way as described above for comparing a test product to a reference product.

A chemically-similar test product and reference product may be tested together by spectrographic analysis. In the example of fuel, to certify a chemically-similar prototype fuel against a reference fuel, a direct match comparison technique may be used. For each certification, a portion of the preserved reference fuel sample may be obtained from a sealed container or from a piston type or water displacement system. Both the reference fuel and prototype fuel may be chilled in the same way prior to testing. For example, the temperature may be greater than 0° C. (32° F.) but not exceed 10° C. (50° F.). All comparisons may be accomplished using a single globally-calibrated spectrometer. Alternatively, different globally-calibrated spectrometers may be used. The reference fuel and prototype fuel may be tested in sequence for one or more cycles, e.g., 10 cycles.

The direct match comparison technique may further comprise calculating the delta between the spectrographically-determined values for the prototype fuel and the reference fuel with respect to each property:

$$\Delta_i = PI_i - RI_i \quad \text{(Equation 3)}$$

Where:
$\Delta_i$=difference between the spectrographically-determined property values of the prototype fuel and the reference fuel
$PI_i$=spectrographically-determined property value of the prototype fuel (text index)
$RI_i$=spectrographically-determined property value of the reference fuel (reference index)
i=a property, such as MON or RON The method may further comprise calculating the derived property of the prototype fuel ($P_i$):

$$P_i = \Delta_i + R_i \quad \text{(Equation 4)}$$

Where:
$P_i$=derived property value of the prototype fuel for certification
$R_i$=property value of the reference fuel determined by primary testing (e.g., consensus value, laboratory reference value or semi-consensus value)

Thus, the direct match comparison technique may comprise adding the delta ($\Delta_i$) to the property value the reference fuel determined by primary testing ($R_i$) to establish the property value of the prototype fuel that may be used for certification against the reference fuel. In various embodiments, $R_i$ may comprise the consensus value, the laboratory reference value or semi-consensus value of the reference fuel.

Figure 4:
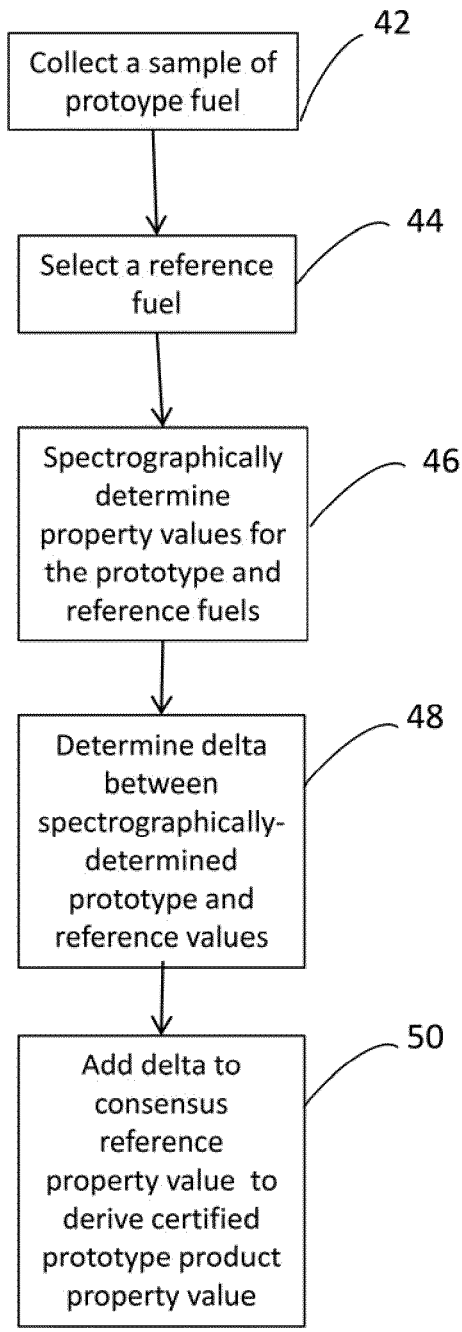
FIG. 4 depicts one embodiment of a method for direct match comparison of a prototype product to a reference product.

FIG. 4 illustrates an exemplary embodiment of a method for direct match comparison of a prototype fuel against a chemically-similar reference fuel. In a step 42, a sample of a prototype fuel for which analysis of a property value is desired may be collected. In a step 44, a reference fuel may be selected for use in a direct match analysis of the prototype fuel. The prototype fuel may be chemically similar to the reference fuel. Chemical similarity may be determined in the manner discussed in more detail above.

In a step 46, a refinery's laboratory may run a spectrographic test of the prototype fuel and the reference fuel using a globally-calibrated spectrometer. The selected reference fuel and the prototype fuel may be measured in a spectrographic analyzer any number of times. As shown in Table 3 (below), sequential spectrographic measurements of the prototype and reference sample may be executed 10 times.

In a step 48, the deltas between the determined property values of the reference fuel and the prototype fuel may be calculated and averaged. For example, the average delta for the RON value associated with ten sequential measurements of the prototype and reference sample in this example may be 0.14. The average delta for the MON values may be 0.24.

In step 50, the average delta values may be added to the consensus value of a property for the reference sample. For example, in the example in Table 3, consensus values of 92.16 for RON and 82.25 for MON may have been previously determined, such as by measurement of the reference sample by a number of external laboratories. Addition of the average deltas to the consensus value may be then be used to determine the certified value of the prototype fuel. For example, for RON addition of the average delta value of 0.14 to the RON consensus value of 92.16 yields a certified value of 92.30. For MON addition of the average delta value of 0.24 to the MON consensus value of 82.25 yields a certified value of 82.49.

TABLE 3

| Spectroscopic RON Prototype Fuel | Spectroscopic RON Reference Fuel | RON Delta | Spectroscopic MON PROTO | Spectroscopic MON Reference Fuel | MON Delta |
| --- | --- | --- | --- | --- | --- |
| 91.9 | 91.88 | 0.02 | 82.39 | 82.15 | 0.24 |
| 92.14 | 92 | 0.14 | 82.31 | 82.14 | 0.17 |
| 92.15 | 91.89 | 0.26 | 82.47 | 82.25 | 0.22 |
| 91.9 | 91.8 | 0.1 | 82.34 | 82.23 | 0.11 |
| 92.07 | 91.82 | 0.25 | 82.23 | 82.00 | 0.23 |

TABLE 3-continued

| Spectroscopic RON Prototype Fuel | Spectroscopic RON Reference Fuel | RON Delta | Spectroscopic MON PROTO | Spectroscopic MON Reference Fuel | MON Delta |
|---|---|---|---|---|---|
| 92.03 | 91.94 | 0.09 | 82.33 | 82.22 | 0.11 |
| 92.13 | 91.88 | 0.25 | 82.38 | 82.00 | 0.38 |
| 91.94 | 91.94 | 0 | 82.46 | 82.12 | 0.34 |
| 91.89 | 91.87 | 0.02 | 82.40 | 82.00 | 0.40 |
| 92.07 | 91.78 | 0.29 | 82.34 | 82.19 | 0.15 |
| Avg. = 92.02 | Avg. = 91.88 | 0.14 | Avg. = 82.36 | Avg. = 82.13 | 0.24 |
| | Standard Consensus Value | 92.16 | | Standard Consensus Value | 82.25 |
| | Certified Value | 92.30 | | Certified Value | 82.49 |

Once a prototype fuel has been certified, it may be used for testing against a chemically similar test product having unknown property values. For example, as discussed above, a prototype fuel may be used for on-line analysis. Thus, a test product may be tested against either or both of a reference or prototype product.

Figure 5:
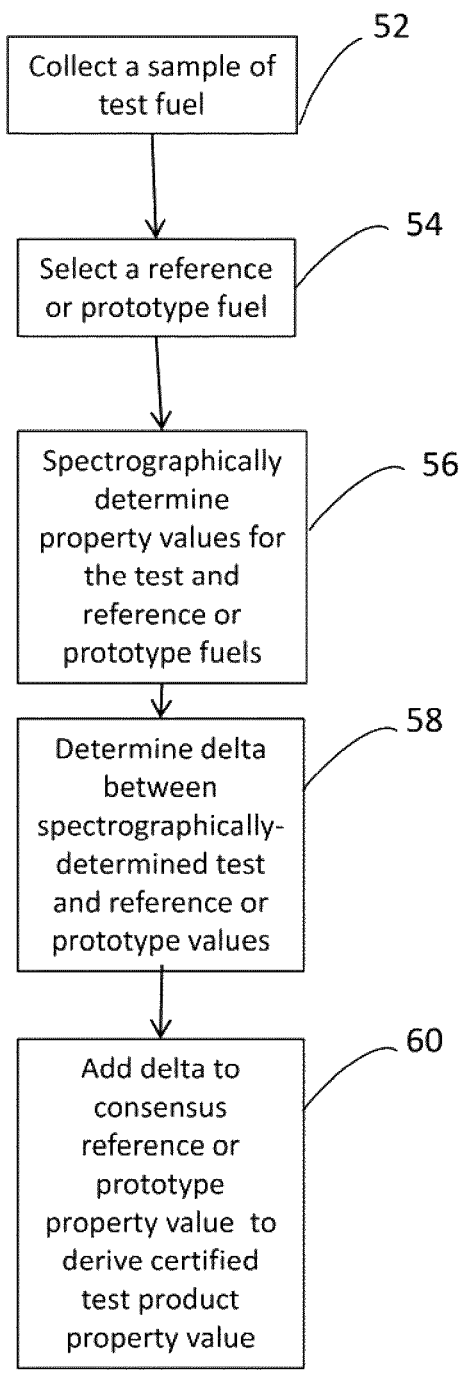
FIG. 5 depicts one embodiment of a method for direct match comparison of a test product to a reference product or prototype product.

FIG. 5 illustrates an exemplary embodiment of a method for direct match comparison of a test fuel against a chemically-similar reference or prototype fuel. In a step 52, a sample of a test fuel for which analysis of a property value is desired may be collected. In a step 54, a reference or prototype fuel may be selected for use in a direct match analysis of the test fuel. The test fuel may be chemically similar to the reference or prototype fuel. Chemical similarity may be determined in the manner discussed in more detail above. In a step 56, a refinery's laboratory may run a spectrographic test of the test fuel and the reference or prototype fuel using a globally-calibrated spectrometer. In step 58, the differences, or deltas, between the spectrographically-determined test and reference or prototype values may be calculated. In step 60, the property value deltas may be added to the reference consensus property values to derive the property values of the test fuel suitable for certification.

Figure 6:
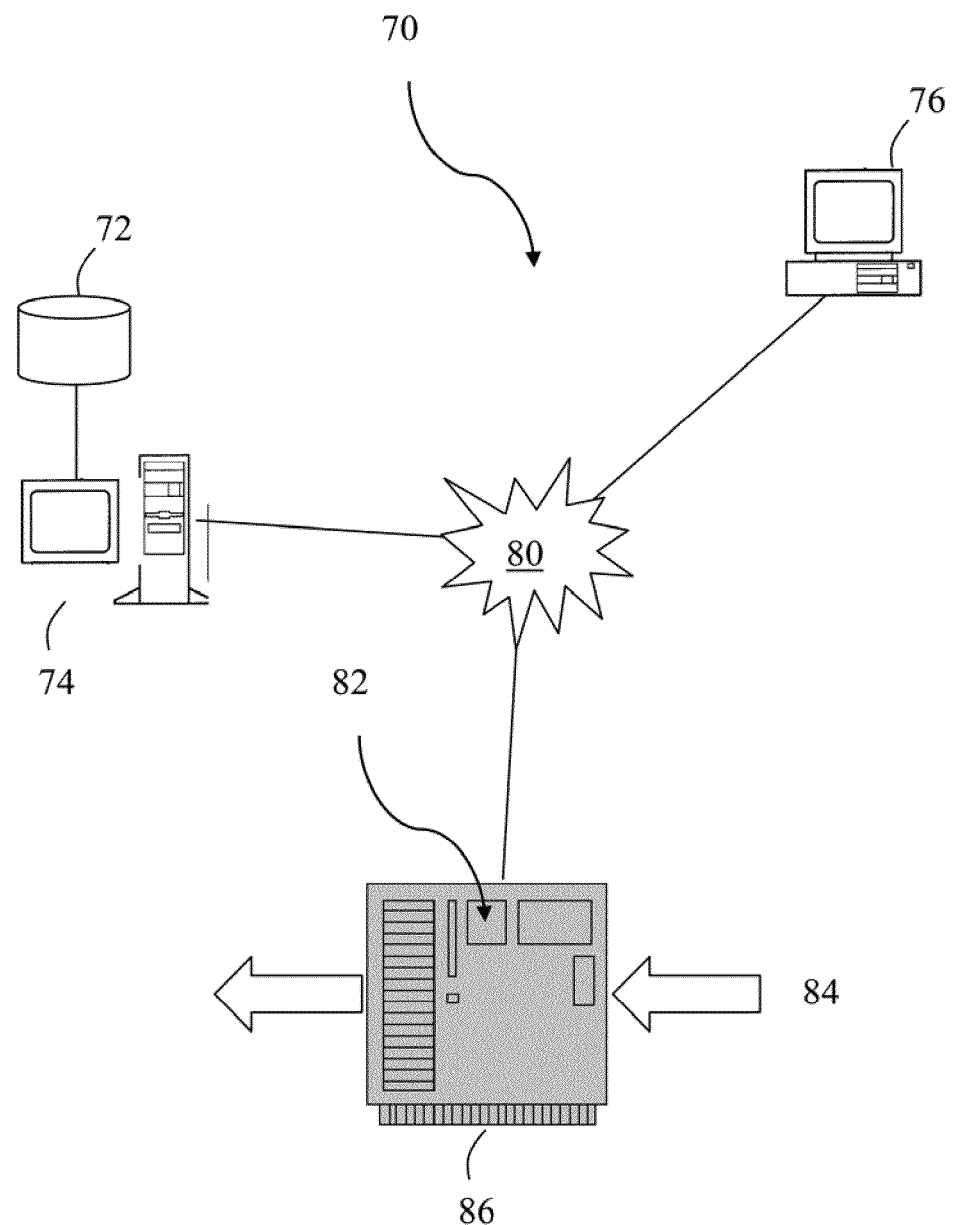
FIG. 6 depicts one embodiment of a system for performing a direct match comparison.

FIG. 6 illustrates one embodiment of a system 70 for direct match comparison. The system may comprise a spectrographic analyzer 86 capable of wireless or wired communication with a computer 76 and server 74 via network 80. The server 74 may be connected to a database 72. The spectrographic analyzer 86 may be an on-line analyzer connected so as to allow collection of a sample 82 of a product stream 84. Alternatively, the spectrographic analyzer 86 may be a standalone device in a refinery laboratory or an outside laboratory. The spectrographic analyzer 86 may be globally-calibrated as described above. In other embodiments, for example, global calibration data may be stored in the database 72. Reference values (e.g., consensus, semi-consensus and laboratory reference values) determined by primary testing, such as engine testing, may be stored in the database 72.

For direct match comparison of a test product to a reference or prototype product, or comparison of a prototype product to a reference product, the spectrographic analyzer 86 may be used to spectrographically determine one or more property values of the test, prototype and/or reference product, as the case may be. In the example of a direct match comparison between a test product and a reference product, the spectrographically-determined reference property value and spectrographically-determined test property value may be communicated to the computer 76, which may be programmed with the algorithms discussed above to determine the delta between the two values. The computer 76 may be further programmed to request and receive a reference consensus value for the property from the database 72 via server 74. The computer 76 may be further programmed to add the delta to the consensus value to derive the certified value of the test product.

The computer 76 may also be programmed to determine a laboratory reference value or a semi-consensus reference value as described above. In some embodiments, the spectrographic analyzer 86 (which may or may not be globally calibrated for this example) may be used to perform multiple property value tests on a reference product sample, and send the test data to the computer 76. The computer 76 may be programmed to statistically treat the data as described above to determine a laboratory reference value. In other embodiments, the computer 76 may be programmed to combine the test data from the spectrographic analyzer 86 with data from outside laboratories, and statistically treat the data as described above to determine a semi-consensus reference value.

In the embodiment of FIG. 6, the system 70 may comprise a client-server architecture. Of course, the system 70 may comprise more than one server and/or client. In other embodiments, the system 70 may comprise other types of network architecture, such as a peer-to-peer architecture, or any combination or hybrid thereof.

The server 74 may comprise one or more computers or programs that respond to commands or requests from one or more other computers or programs, or clients. The client 76 may comprise one or more computers or programs that issue commands or requests for service provided by one or more other computers or programs, or servers. The server 74 and client 76 may be located in or across one or more computers and/or geographic locations. Servers and/or clients may variously be or reside on, for example, mainframe computers, desktop computers, PDAs, smartphones (such as Apple's iPhone™, Motorola's Atrix™ 4G, and Research In Motion's Blackberry™ devices), tablets, netbooks, portable computers, portable media players with network communication capabilities (such as Microsoft's Zune HD™ and Apple's iPod Touch™ devices), cameras with network communication capabilities, wearable computers, point of sale devices, spectrographic analyzers, and the like.

A computer may be any device capable of accepting input, processing the input according to a program, and producing output. A computer may comprise, for example, a processor, memory and network connection capability. Computers may be of a variety of classes, such as supercomputers, mainframes, workstations, microcomputers, and PDAs, according to the computer's size, speed, cost and abilities. Computers may be stationary or portable, and may be programmed for a variety of functions, such as cellular telephony, media recordation and playback, data transfer, web browsing, data processing, data query, process automation, video conferencing, artificial intelligence, and much more.

A program may comprise any sequence of instructions, such as an algorithm, whether in a form that can be executed by a computer (object code), in a form that can be read by humans (source code), or otherwise. A program may comprise or call one or more data structures and variables. A program may be embodied in hardware or software, or a combination thereof. A program may be created using any suitable programming language, such as C, C++, Java, Perl, PHP, Ruby, SQL, and others. Computer software may comprise one or more programs and related data. Examples of computer software include system software (such as operating system software, device drivers and utilities), middleware (such as web servers, data access software and enterprise messaging software), application software (such as databases, video games and media players), firmware (such as software installed on calculators, keyboards and mobile phones), and programming tools (such as debuggers, compilers and text editors).

Memory may comprise any computer-readable medium in which information can be temporarily or permanently stored and retrieved. Examples of memory include various types of RAM and ROM, such as SRAM, DRAM, Z-RAM, flash, optical disks, magnetic tape, punch cards, EEPROM. Memory may be virtualized, and may be provided in or across one or more devices and/or geographic locations, such as RAID technology.

An I/O device may comprise any hardware that can be used to provide information to and/or receive information from a computer. Exemplary I/O devices include disk drives, keyboards, video display screens, mouse pointers, printers, card readers, scanners (such as barcode, fingerprint, iris, QR code, and other types of scanners), RFID devices, tape drives, touch screens, cameras, movement sensors, network cards, storage devices, microphones, audio speakers, styli and transducers, and associated interfaces and drivers.

A network may comprise a cellular network, the Internet, intranet, local area network (LAN), wide area network (WAN), Metropolitan Area Network (MAN), other types of area networks, cable television network, satellite network, telephone network, public networks, private networks, wired or wireless networks, virtual, switched, routed, fully connected, and any combination and subnetwork thereof. The network may use a variety of network devices, such as routers, bridges, switches, hubs, repeaters, converters, receivers, proxies, firewalls, translators and the like. Network connections may be wired or wireless, and may use multiplexers, network interface cards, modems, IDSN terminal adapters, line drivers, and the like. The network may comprise any suitable topology, such as point-to-point, bus, star, tree, mesh, ring and any combination or hybrid thereof.

Communication in and among computers, I/O devices and network devices may be accomplished using a variety of protocols. Protocols may include, for example, signaling, error detection and correction, data formatting and address mapping. For example, protocols may be provided according to the seven-layer Open Systems Interconnection model (OSI model), or the TCP/IP model.

In other embodiments, a computer may be programmed to store primary test reference values in its memory and/or retrieve such values from a database. The computer may be programmed to programmed to receive (1) a property value of a first refinery product, such as a reference fuel, the property value determined using a non-spectrographic test, (2) a property value of the first refinery product determined using a spectrographic analyzer, and (3) a property value of a second refinery product determined using the spectrographic analyzer. The computer may be further programmed to determine a difference between the spectrographically-determined property values of the first refinery product and the second refinery product; and to add the difference to the non-spectrographically-determined property value of the first refinery product to derive a property value for the second refinery product.

In yet other embodiments, a spectrographic analyzer may be configured to receive a property value of a first refinery product using a non-spectrographic test; determine a property value of the first refinery product using a first globally-calibrated spectrographic analyzer; determine a property value of a second refinery product; determine a difference between the spectrographically-determined property values of the first refinery product and the second refinery product; and add the difference to the non-spectrographically-determined property value of the first refinery product to derive a property value for the second refinery product.

In yet other embodiments, a system may be provided for direct match comparison. The system may comprise a spectrographic analyzer capable of determining a property value of a first refinery product, and determining a property value of a second refinery product. The system may further comprise a computer programmed to receive a property value of the first refinery product, the property value determined using a non-spectrographic test, and to receive the property values of the first and second refinery products determined by the spectrographic analyzer. The computer may be further programmed to determine a difference between the spectrographically-determined property values of the first refinery product and the second refinery product, and add the difference to the non-spectrographically-determined property value of the first refinery product to derive a property value for the second refinery product.

Improved precision (e.g., reduced test variation) provided by use of spectrometers, may result in a variety of benefits to refineries. One benefit may be better risk management. Improved precision may significantly lower the probability of shipping a product that does not materially conform to product specifications, even if tests of the product show material conformance with such specifications. For example, improved precision may result in reducing test variation from approximately 1 error in approximately 20 tests to approximately 1 error in approximately 1000 tests.

Another benefit may be better economics. Reduced variation may allow the product producer to better target a product property value more closely to a product specification, thus reducing property giveaway.

When a spectrographic analysis is done, the resulting data for a test fuel may be tested against a reference fuel that may have similar properties (chemical similarity) to the fuel being tested. In some embodiments, the test fuel may have certified properties that are no more than one degree of separation from a reference fuel, i.e., the test fuel is referenced against a prototype fuel that may itself be tested against a reference fuel. The test result of an unknown fuel may be the determined property value of the test fuel, which may be calculated by subtracting by the spectrographically-determined property of the reference fuel from the spectrographically-determined property of the test fuel (the $\Delta$), and adding the delta to the consensus value of the reference fuel.

Although the present invention and its advantages have been described in detail, it should be understood that various changes, substitutions and alterations can be made herein without departing from the invention as defined by the appended claims. Moreover, the scope of the present application is not intended to be limited to the particular embodiments of the process, machine, manufacture, composition, or matter, means, methods and steps described in the specification. As one will readily appreciate from the disclosure, processes, machines, manufacture, compositions of matter, means, methods, or steps, presently existing or later to be developed that perform substantially the same function or achieve substantially the same result as the corresponding embodiments described herein may be utilized. Accordingly, the appended claims are intended to include within their scope such processes, machines, manufacture, compositions of matter, means, methods or steps.

I claim:

1. A method for deriving a refinery product property value, the method comprising:
    determining a property value of a first refinery product using a non-spectrographic test;
    determining a property value of the first refinery product using a first globally-calibrated spectrographic analyzer;
    determining a property value of a second refinery product using a second globally-calibrated spectrographic analyzer;
    determining a difference between the spectrographically-determined property values of the first refinery product and the second refinery product;
    adding the difference to the non-spectrographically-determined property value of the first refinery product to derive a property value for the second refinery product.

2. The method of claim 1, wherein the spectrographic analysis involves using at least one of Near Infrared (NIR), Mid Infrared (MIR), Near and Mid (full range) Infrared (IR), Fourier Transform Near Infrared (FTNIR), Fourier Transform Mid Infrared (FTMIR), Fourier Transform Near and Mid (full range) Infrared (FTIR), Nuclear Magnetic Resonance (NMR) and Raman.

3. The method of claim 1 wherein the first globally-calibrated spectrographic analyzer and second globally-calibrated spectrographic analyzer comprise the same instrument.

4. The method of claim 1 wherein the refinery product comprises fuel.

5. The method of claim 4 wherein the refinery product comprises at least one of spark-ignited fuel, distillate fuel and turbine fuel.

6. The method of claim 5, wherein the product property comprises at least one of RON, MON, RVP, T(v/l)=20, specific gravity, aromatics, polynuclear aromatics, olefins, benzene, oxygen, ethanol, distillation, flash, viscosity, analine point and cetane number.

7. The method of claim 1 wherein the refinery product comprises lubricating oil.

8. The method of claim 1 wherein the first refinery product and the second refinery product are chemically similar.

9. The method of claim 1 wherein the first refinery product comprises a reference product and the second refinery product comprises a test product having an unknown property value.

10. The method of claim 1 wherein the first refinery product comprises a reference product and the second refinery product comprises a prototype product having an unknown property value.

11. The method of claim 1 wherein determining a property value of the first refinery product using a first globally-calibrated spectrographic analyzer comprises determining one of a consensus value, a laboratory reference value and a semi-consensus value.

12. The method of claim 1 wherein the global calibration of the first and second globally-calibrated spectrographic analyzers is based on a plurality of location-specific refinery product data.

13. The method of claim 12 wherein the location-specific refinery product data comprises data from at least two refineries, each separated geographically from one another.

14. The method of claim 1 wherein the global calibration of the first and second globally-calibrated spectrographic analyzers is based on a plurality of matrix-specific refinery product data.

15. The method of claim 14 wherein the matrix-specific refinery product data comprises data characterizing at least one of a spark-ignition fuel product, a distillate fuel product and a turbine fuel product.

16. The method of claim 1 wherein the global calibration of the first and second globally-calibrated spectrographic analyzers is based on a plurality of location-specific and matrix-specific refinery product data.

17. An apparatus for direct match comparison, the apparatus comprising a spectrographic analyzer capable of receiving a property value of a first refinery product determined using a non-spectrographic test; determining a property value of the first refinery product using a first globally-calibrated spectrographic analyzer; determining a property value of a second refinery product; determining a difference between the spectrographically-determined property values of the first refinery product and the second refinery product; and adding the difference to the non-spectrographically-determined property value of the first refinery product to derive a property value for the second refinery product.

18. A system for direct match comparison, the system comprising:
    a spectrographic analyzer capable of determining a property value of a first refinery product, and determining a property value of a second refinery product; and
    a computer programmed to receive a property value of the first refinery product, the property value determined using a non-spectrographic test; receive the property values of the first and second refinery products determined by the spectrographic analyzer; determine a difference between the spectrographically-determined property values of the first refinery product and the second refinery product; and add the difference to the non-spectrographically-determined property value of the first refinery product to derive a property value for the second refinery product.

19. An apparatus for direct match comparison, the apparatus comprising a computer programmed (A) to receive (1) a property value of a first refinery product, the property value determined using a non-spectrographic test, (2) a property value of the first refinery product determined using a spectrographic analyzer, and (3) a property value of a second refinery product determined using the spectrographic analyzer; (B) to determine a difference between the spectrographically-determined property values of the first refinery product and the second refinery product; and (C) add the difference to the non-spectrographically-determined property value of the first refinery product to derive a property value for the second refinery product.

* * * * *

UNITED STATES PATENT AND TRADEMARK OFFICE
CERTIFICATE OF CORRECTION

PATENT NO. : 8,481,942 B2  
APPLICATION NO. : 13/084500  
DATED : July 9, 2013  
INVENTOR(S) : Daniel C. Mertens Page 1 of 1

It is certified that error appears in the above-identified patent and that said Letters Patent is hereby corrected as shown below:

In the Specification

In column 7, line 46, replace "nm" with --run--;
In column 17, line 61, delete duplicate "programmed to".

Signed and Sealed this
Twentieth Day of August, 2013

Teresa Stanek Rea
*Acting Director of the United States Patent and Trademark Office*